(12) United States Patent
Goeders et al.

(10) Patent No.: US 10,119,913 B2
(45) Date of Patent: *Nov. 6, 2018

(54) DIE-INTEGRATED ASPHERIC MIRROR

(71) Applicant: Honeywell International Inc., Morris Plains, NJ (US)

(72) Inventors: James Edward Goeders, Plymouth, MN (US); Matthew Edward Lewis Jungwirth, Golden Valley, MN (US); Terry Dean Stark, St. Louis Park, MN (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/687,688

(22) Filed: Aug. 28, 2017

(65) Prior Publication Data

US 2018/0003636 A1 Jan. 4, 2018

Related U.S. Application Data

(63) Continuation of application No. 14/686,524, filed on Apr. 14, 2015, now Pat. No. 9,791,370.

(51) Int. Cl.
| | |
|---|---|
| *G01N 21/64* | (2006.01) |
| *G02B 5/10* | (2006.01) |
| *G02B 17/06* | (2006.01) |
| *G06N 99/00* | (2010.01) |

(Continued)

(52) U.S. Cl.
CPC ..... *G01N 21/6456* (2013.01); *G01N 21/6404* (2013.01); *G02B 5/10* (2013.01); *G02B 17/0605* (2013.01); *G06N 99/002* (2013.01);

*H01J 3/16* (2013.01); *B82Y 10/00* (2013.01); *G01N 2021/6469* (2013.01); *G01N 2021/6484* (2013.01)

(58) Field of Classification Search
CPC ........... G01N 21/6456; G01N 21/6402; G01N 21/6404; G01N 2021/6469; G01N 2021/6484; G02B 5/10; G02B 17/0605; G06N 99/002; H01J 3/16; H01J 49/4225; B82Y 10/00
USPC .......................................... 250/458.1, 492.1
See application file for complete search history.

(56) References Cited

U.S. PATENT DOCUMENTS

| | | |
|---|---|---|
| 5,389,784 A | 2/1995 | Weller |
| 5,679,950 A | 10/1997 | Baba et al. |

(Continued)

FOREIGN PATENT DOCUMENTS

CN 102519928 B 5/2013

OTHER PUBLICATIONS

Shu, G. et al., 2011, "Efficient fluorescence collection and ion imaging with the "tack" ion trap", arxiv.org, Cornell University Library, pp. 1-9.*

(Continued)

*Primary Examiner* — David Porta
*Assistant Examiner* — Blake Riddick
(74) *Attorney, Agent, or Firm* — Brooks, Cameron & Huebsch, PLLC (57) ABSTRACT

Apparatuses and systems for a die-integrated aspheric mirror are described herein. One apparatus includes an ion trap die including a number of ion locations and an aspheric mirror integrated with the ion trap die.

20 Claims, 3 Drawing Sheets

(51) Int. Cl.
*H01J 3/16* (2006.01)
*B82Y 10/00* (2011.01)

(56) References Cited

U.S. PATENT DOCUMENTS

| | | | | |
|---|---|---|---|---|
| 5,793,091 | A * | 8/1998 | Devoe | G06N 99/002 |
| | | | | 257/17 |
| 6,728,281 | B1 | 4/2004 | Santori et al. | |
| 7,180,078 | B2 | 2/2007 | Pau et al. | |
| 7,411,187 | B2 | 8/2008 | Monroe et al. | |
| 7,807,963 | B1 | 10/2010 | Bier | |
| 7,859,350 | B1 | 12/2010 | Schwindt | |
| 8,395,112 | B1 * | 3/2013 | Bier | G01N 21/53 |
| | | | | 250/281 |
| 8,512,538 | B2 | 8/2013 | Majlof et al. | |
| 2003/0231828 | A1 * | 12/2003 | Brock | G02B 6/42 |
| | | | | 385/33 |
| 2006/0169882 | A1 * | 8/2006 | Pau | G21K 1/003 |
| | | | | 250/281 |
| 2007/0252081 | A1 | 11/2007 | Munro et al. | |
| 2009/0135460 | A1 | 5/2009 | Kim | |
| 2009/0213444 | A1 | 8/2009 | Goto et al. | |
| 2010/0019136 | A1 | 1/2010 | Merenda et al. | |
| 2011/0036995 | A1 | 2/2011 | Binnie et al. | |
| 2014/0004559 | A1 | 1/2014 | Hill et al. | |
| 2016/0072585 | A1 * | 3/2016 | Halderman | G02B 6/4204 |
| | | | | 398/141 |

OTHER PUBLICATIONS

Maiwald, R. et al., 2012, "Collecting more than half the fluorescence photons from a single ion", Physical Review A, col. 86, pp. 043431-1-043431-5.*

Extended Search Report from related European Patent Application No. 16154682, dated Aug. 18, 2016, 10 pp.

Maiwald, et al., "Ion traps with enhanced optical and physical access", arxiv.org, Cornell University Library, dated Mar. 19, 2009, 6 pp.

Shu, et al., "Efficient fluorescence collection and ion imaging with the "tack" ion trap", arxiv.org, Cornell University Library, dated Aug. 29, 2011, 9 pp.

Shu, et al., "Trapped ion imaging with a high numerical aperture spherical mirror", Journal of Physics B: Atomic, Molecular and Optical Physics, Jul. 15, 2009, 5 pp.

Bondo, et al., "Time-resolved and state-selective detection of single freely falling atoms", Optics Communications, vol. 264, No. 2, Aug. 15, 2006, 7 pp.

J True Merrill, et al. "Demonstation of integrated microscale optics in surface-electrode ion traps". 2011 New J. Phys. 13. Accessed from http://iopscience.iop.org/1367-2630/13/10/103005/fulltext/. 17 pages.

Trautmann, N. et al., 2014, "Generation of entangled matter qubits in two opposing parabolic mirrors", Physical Review A, vol. 90, pp. 063814-1-063814-9.

* cited by examiner

DIE-INTEGRATED ASPHERIC MIRROR

PRIORITY INFORMATION

This application is a continuation of U.S. Non-Provisional application Ser. No. 14/686,524, filed Apr. 14, 2015, the contents of which are incorporated herein by reference.

STATEMENT OF GOVERNMENT RIGHTS

The subject matter of this disclosure was made with government support under the Government Program Jayhawk under Contract No. 7004639708. Accordingly, the U.S. government has certain rights to subject matter disclosed herein.

TECHNICAL FIELD

The present disclosure relates to apparatuses and systems having a die-integrated aspheric mirror, for example, for increased collection of fluorescent light.

BACKGROUND

Quantum state detection efficiency relies on the efficiency of the collection of light fluorescence from optical systems. Fluorescent light collection may, for example, be implemented with bulk optics.

For instance, fluorescent light collection may involve placing a high numerical aperture objective near a fluorescence point source (e.g., an atomic ion) and detecting emitted fluorescent light (e.g., photons) outside of a vacuum chamber, whereby the detection may be several inches away. Such a setup may yield a solid angle capture for emitted fluorescent light, for example, of less than 5%.

Collection of fluorescent light using bulk optics may involve careful alignment of optical and other elements (e.g., lasers, lenses, ion traps, etc.). Without this careful alignment, much of the fluorescent light may be lost, thereby contributing to a decrease in quantum state detection efficiency. The use of bulk optical elements also may adversely affect robustness (e.g., to wear, impact, etc.) of a quantum informatics system, possibly limiting use of such systems to research environments.

DETAILED DESCRIPTION

Large planar ion trap systems with many ion zones (locations) for trapping ions, which may be densely packed in operational arrays, may allow for more efficient fluorescent light collection in parallel (e.g., from many ions simultaneously). According to the present disclosure, apparatuses and systems having a die-integrated aspheric mirror can include an ion trap die including a number of ion locations and an aspheric mirror integrated (e.g., physically integrated) with the ion trap die for increased collection of fluorescent light.

In the following detailed description, reference is made to the accompanying figures that form a part hereof. The figures show by way of illustration how one or more embodiments of the disclosure may be practiced.

The figures herein follow a numbering convention in which the first digit or digits correspond to the drawing figure number and the remaining digits identify an element or component in the drawing. Similar elements or components between different figures may be identified by the use of similar digits. For example, 109 may reference element "09" in FIG. 1, and a similar element may be referenced as 209 in FIG. 2.

Figure 1:
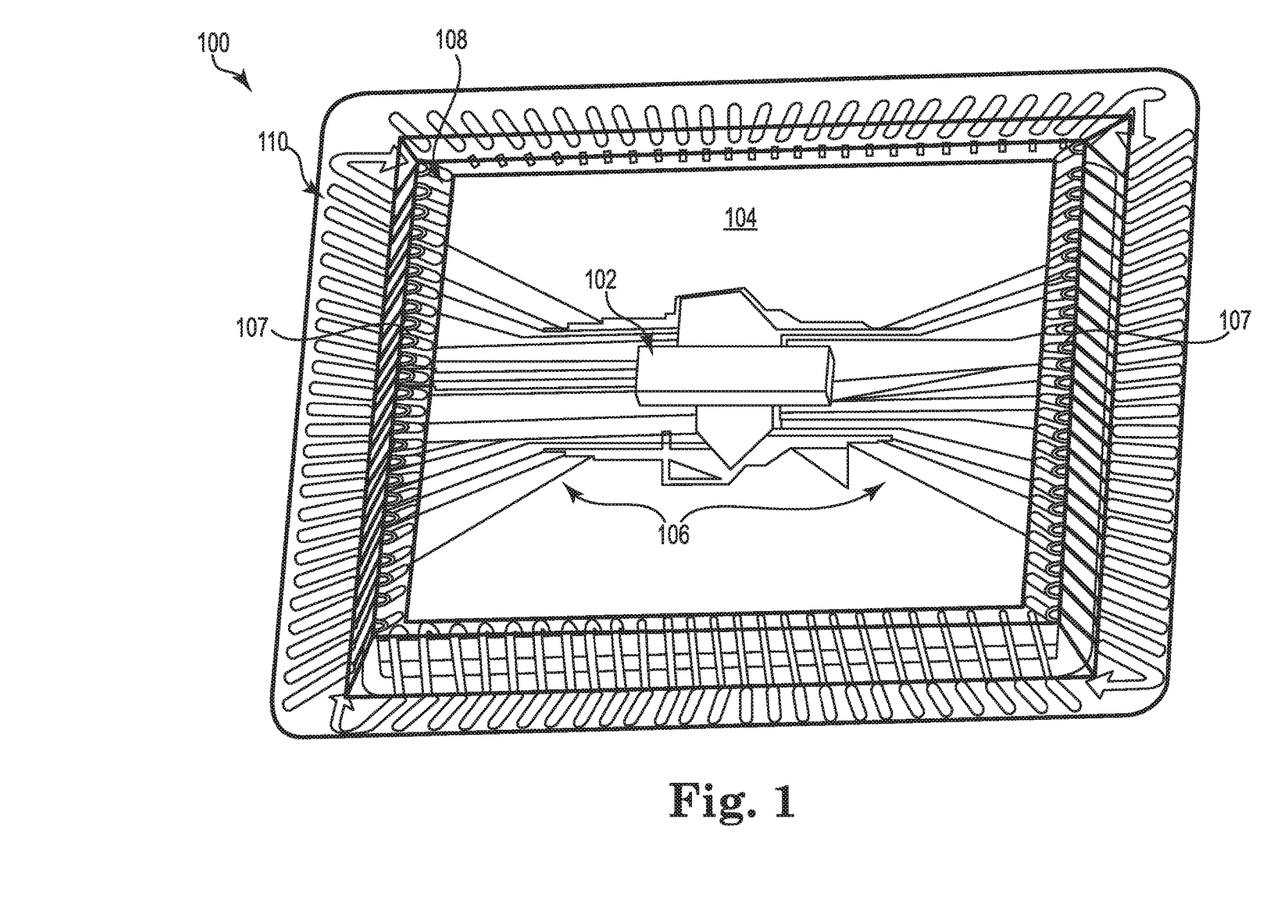
FIG. 1 illustrates a portion of a fluorescent light collection system in accordance with one or more embodiments of the present disclosure.

FIG. 1 illustrates a portion of a fluorescent light collection system in accordance with one or more embodiments of the present disclosure. The embodiment of the fluorescent light collection system 100 shown in FIG. 1 can include at least one ion trap die 102. The ion trap die 102 can be configured to trap (capture) a charged atom or molecule (ion) in each ion location (potential well) that is capable of emitting fluorescent light (one or more photons) after excitation by a light source (not shown).

In some embodiments, the light source can be a laser tuned to emit a specific frequency range for excitation of a particular electron transition of a particular element to emit fluorescent light in a particular frequency and/or wavelength range. Depending upon the implementation, the laser can be tuned to emit a frequency range narrow enough to promote emission of fluorescent light in a narrow frequency and/or wavelength range by the particular ion.

The ion trap die 102 can be integrated with (e.g., connected to and/or mounted on) an underlying planar surface 104. In various embodiments, the underlying planar surface 104 can be a top surface of an interposer die 110, as described herein, or an intermediate die 108.

The intermediate die 108 can, in some embodiments, be utilized to provide structural spacing for integration of an aspheric mirror, as described herein, between circuitry of the interposer die 110 and the underlying planar surface 104 upon which the ion trap die 102 is integrated. In some embodiments, the intermediate die 108 and the interposer die 110 can be combined into one die.

The intermediate die 108 and/or the interposer die 110 can be configured to provide electrical leads 106 to empower various functionalities associated with the ion trap die 102. The electrical leads 106 can be directed to the ion trap die 102 and/or the various functionalities associated therewith by transiting from a source (not shown) of electrical power and/or electronic (e.g., digital) instructions beneath the underlying planar surface 104 upon which the ion trap die 102 is integrated.

In some embodiments, the electrical leads 106 can each be connected by a wire bond at a connection point 107 in the intermediate die 108 and/or the interposer die 110 so as to be electrically connected to the source. The number and/or positioning of the electrical leads 106 and/or connection points 107 are shown by way of illustration.

That is, consistent with the present disclosure, more or less electrical leads 106 and/or connection points 107 can be utilized, which can be integrated at various positions with regard to the intermediate die 108 and/or the interposer die 110. Accordingly, such configurations for the electrical leads 106 and/or connection points 107 can enable unobstructed optical transit of light directed toward and/or emitted from the ion trap die 102.

Ion traps can use a combination of electrical and/or magnetic fields to capture an ion (e.g., an ytterbium ion ($Yb^+$), among other possible positive and/or negative ions of atomic and/or molecular species) in a potential well. However, ion traps may be space limited due to electrical and/or electronic components (e.g., capacitors, resistors, transistors, etc.) that enable functionality of the ion trap by being positioned on the same die as the ion trap (being on-chip) and/or optically limited due to electrical leads, wire bonds, etc., being positioned to obstruct a beam path of a light source utilized for ion excitation and/or a potential pathway for fluorescent light emitted by the ions.

Accordingly, to overcome such potential difficulties, a number of ion traps can be formulated in an ion trap die, for example, as shown at 102 in the embodiment illustrated in FIG. 1. The ion trap die 102 can, for example, include integrated trench capacitors and/or through-silicon-vias to replace capacitors, electrical leads, and/or wire bonds, etc., otherwise possibly positioned on a surrounding surface. The ion trap die 102 shown in FIG. 1 can be integrated with the intermediate die 108 and/or the interposer die 110 using the through-silicon-vias.

The intermediate die 108 and/or the interposer die 110 can, in various embodiments, contain and/or direct a configuration (e.g., a fan out) of electrical leads 106 that transit from the ion trap die 102 to an outer edge of the intermediate die 108 and/or the interposer die 110. At or near the outer edge of the intermediate die 108 and/or the interposer die 110, wire bonds at connection points 107 can, in various embodiments, be used to connect the electrical leads 106 to the source (not shown) of electrical power and/or electronic (e.g., digital) instructions beneath the underlying planar surface 104 upon which the ion trap die 102 is integrated. In some embodiments, such a source can be a processor and/or controller of a processing system, as described herein.

The just-described structure can yield a number of benefits. For example, the structure can provide full optical access to the ion trap die 102 and/or the particular positions of the ion locations fabricated therein.

Mounting the ion trap die 102 on the planar surface 104 of the intermediate die 108 and/or the interposer die 110 can be beneficial in that it can enable removal of wire bonds of the electrical leads from edges of the ion trap die 102 by moving the wire bonds to connection points 107 to the outer edge of the intermediate die 108 and/or the interposer die 110. The ion trap die 102 being raised above the level of the wire bonds and/or positioned on the planar surface 104 interior to the wire bonds can be beneficial in that it can contribute to providing optical access from any direction (27) around a perimeter of the ion trap die 102 and/or the particular positions of the ion locations.

Another benefit can be integrating, for example, filter and/or trench capacitors onto and/or into the ion trap die 102, which can enable a reduction in a size of the ion trap die (e.g., by a factor of 30 or so). Accordingly, the reduction in size for each ion trap die can result in free space (area) on the planar surface 104 of the intermediate die 108 and/or the interposer die 110. Benefits of such free space can include mounting additional ion trap dies on the same area of the planar surface 104, among other possible benefits of the free space.

Figure 2:
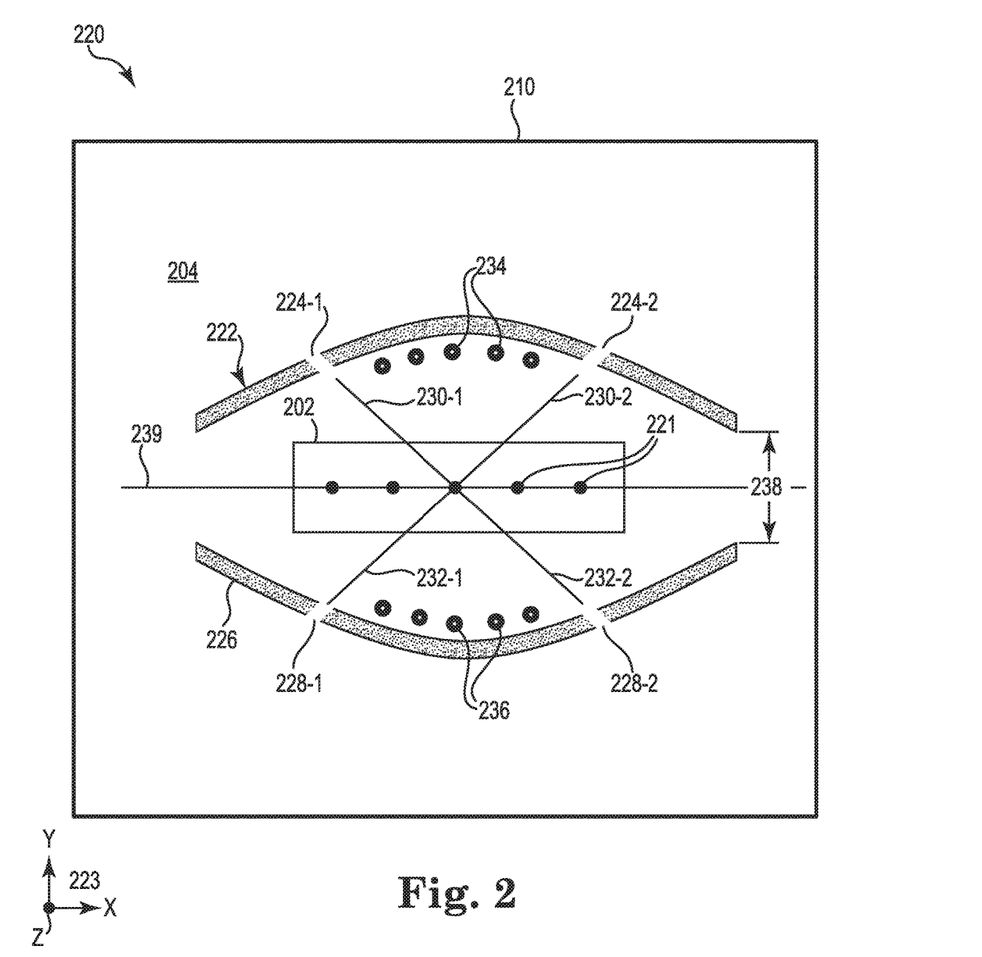
FIG. 2 illustrates a die-integrated aspheric mirror system in accordance with one or more embodiments of the present disclosure.

FIG. 2 illustrates a die-integrated aspheric mirror system in accordance with one or more embodiments of the present disclosure. As described herein, the die-integrated aspheric mirror system 220 illustrated in FIG. 2 can, in various embodiments, be integrated with the portion of the fluorescent light collection system 100 illustrated in FIG. 1. The elements shown in FIGS. 1 and 2 are not necessarily representative of their proportion and/or their relative scale in actual fabrication and are intended to illustrate the embodiments of the present disclosure, and should not be taken in a limiting sense.

The embodiment of the die-integrated aspheric mirror system 220 illustrated in FIG. 2 shows an ion trap die 202. In various embodiments, the ion trap die 202 can be fabricated to include a plurality of ion locations 221 (potential wells). For example, the ion trap die 202 can include five ion locations 221, as shown in FIG. 2, although embodiments are not so limited.

As described with regard to FIG. 1, the ion trap die 202 can be integrated with an underlying planar surface 204, which, in some embodiments, can be a top surface of an interposer die 210. In some embodiments, interposer die can be fabricated with x and y axes (as shown at 223) in a range of from around 0.5 centimeters (cm) to around 5.0 cm or more. In some embodiments, an intermediate die (shown at 108 in FIG. 1) can be utilized to provide structural spacing for integration of a number of aspheric mirrors 222, 226 between circuitry of the interposer die 210 and the underlying planar surface 204 upon which the ion trap die 202 is integrated.

In some embodiments, an ion trap die 202 can be fabricated with a longitudinal axis (in an x direction as shown at 223 in FIG. 2) in a range of from around 2.0 millimeters (mm) to around 4.0 mm or more, in particular when the ion trap die 202 is fabricated with a plurality of ion locations 221. In some embodiments, an ion trap die 202 can be fabricated with a horizontal axis (in a y direction as shown at 223) in a range of from around 0.5 mm to around 1.5 mm or more. In some embodiments, an ion trap die 202 can be fabricated with a vertical axis (in a z direction perpendicular to an x-y plane as shown at 223) in a range of from around 0.1 mm to around 0.5 mm or more.

To facilitate efficient solid angle capture and reflection of fluorescent light emitted by ions in the plurality of ion locations 221, each aspheric mirror 222, 226 can have a diameter or major axis, depending on the configuration of the aspheric mirror, that is at least as large as the longitudinal axis of the ion trap die 202, for example, as shown in FIG. 2. As such, each aspheric mirror 222, 226 can, in various embodiments, be fabricated with a diameter or major axis (in an x direction as shown at 223 in FIG. 2) in a range of from around 2.0 mm to around 4.0 mm or more, in particular when the ion trap die 202 is fabricated with a plurality of ion locations 221.

In some embodiments, an aspheric mirror can be a glass prism with a reflective surface that is sputtered with aluminum and/or gold, among other possible reflective materials. Such an aspheric mirror may be referred to herein as a "micromirror".

In various embodiments, each aspheric mirror 222, 226 can be integrated into the planar surface 204 of the intermediate die 108 and/or the interposer die 210 such that a diameter or minor axis (in a z direction, into and/or out of the page, as shown at 223 in FIG. 2), depending on the configuration of the aspheric mirror, is substantially perpendicular to the x-y plane of the interposer die 210 and/or the x-y plane of the ion trap die 202. In various embodiments, various positions on a reflective surface of an aspheric mirror 222 may be separated from an associated ion trap die 202 by a distance of 20 mm or more.

Accordingly, a die-integrated aspheric mirror apparatus, as just described, can include an ion trap die 202 including a number of ion locations 221 and an aspheric mirror 222 integrated with the ion trap die 202. The ion trap die 202 and the aspheric mirror 222 can, in various embodiments, both be physically integrated with the substantially planar surface 204 of a substrate die (e.g., the intermediate die 108 and/or the interposer die 110, 210 described herein).

As described herein, an aspheric mirror can be formed to have various contours along the reflective surface so as to have a plurality of image locations. A location of each image location can depend upon a position at which fluorescent light is captured by the reflective surface of the aspheric mirror 222 and/or the ion location 221 from which the fluorescent light is emitted. A direction of an image location relative to a vertical axis (e.g., a major axis and/or a minor axis in the x and/or z directions) of the aspherical mirror 222 can define a principal axis of the aspherical mirror 222. In embodiments in which an aspherical mirror has a plurality of image locations, the aspherical mirror also can have a plurality of principal axes.

Accordingly, in various embodiments, the ion trap die 202 can include a longitudinal axis, as described herein, and the aspheric mirror 222 can be configured to be integrated with the ion trap die 202 such that a principal axis (e.g., at least one principal axis) of the aspheric mirror 222 is substantially aligned with and/or perpendicular to the longitudinal axis of the ion trap die 202. The ion trap die 202 can, in various embodiments, include a horizontal axis, as described herein, and the aspheric mirror 222 can be configured to be integrated with the ion trap die 202 such that a principal axis (e.g., at least one principal axis) of the aspheric mirror 222 is substantially aligned with the horizontal axis of the ion trap die 202.

As described herein, an aspheric mirror can be formed with an ellipsoidal configuration. The ellipsoidal configuration can be tri-axial by having at least three distinct semi-axes. For example, a major axis of the ellipsoidal configuration can, in some embodiments, be substantially parallel to the longitudinal axis of the ion trap die 202 and/or a minor axis of the ellipsoidal configuration can, in some embodiments, be substantially perpendicular to the horizontal axis of the ion trap die 202.

As described in the present disclosure, each aspheric mirror can, in various embodiments, be fabricated with a number of apertures formed to enable light from an outside light source to transit therethrough toward the ion locations 221 in the ion trap die 202. For example, aspheric mirror 222 is shown to have two apertures 224-1, 224-2 and aspheric mirror 226 also is shown to have two apertures 228-1, 228-2, although embodiments are not so limited.

A combination between positioning of one or more light sources (e.g., lasers) and positioning and/or configuration of a number of apertures can enable one or more light beams to be directed toward (e.g., aimed at) a particular ion location (e.g., from a plurality of ion locations). For example, among other possibilities, positioning of the one or more light sources relative to a convex side of aspheric mirror 222 in combination with the positioning and/or configuration of aperture 224-1 can enable light beam 230-1 to be aimed at a middle ion location 221 in ion trap die 202, as can aperture 224-2 with light beam 230-2.

In some embodiments, a second aspheric mirror 226 can be utilized to increase the solid angle capture of emitted fluorescent light. Accordingly, for aspheric mirror 226, positioning of the one or more light sources relative to a convex side of aspheric mirror 226 in combination with the positioning and/or configuration of aperture 228-1 can enable light beam 232-1 to be aimed at the middle ion location 221 in ion trap die 202, as can aperture 228-2 with light beam 232-2.

As described in the present disclosure, each aspheric mirror can have reflective positions and/or contours configured to reflect (e.g., focus) fluorescent light emitted from particular ion locations toward at least one optical fiber. For example, aspheric mirror 222 is shown with optical fibers 234 positioned at intended positions relative to a reflective surface thereof for coupling with fluorescent light captured and reflected by aspheric mirror 222.

Similarly, aspheric mirror 226 is shown with optical fibers 236 positioned at intended positions relative to a reflective surface thereof for coupling with fluorescent light captured and reflected by aspheric mirror 226. Although five optical fibers are illustrated as integrated with each aspheric mirror, embodiments are not so limited.

In various embodiments, the optical fibers 234, 236 can be integrated with the intermediate die 108 and/or the interposer die 210 and extend upward into a cavity in the intermediate die 108 and/or the interposer die 210 (not shown) between a respective aspheric mirror 222, 226 and the ion trap die 202. Such a cavity can enable unobstructed transit of light from the apertures 224-1, 224-2 to the ion locations 221 and/or from the ion locations 221 to the optical fibers 234, 236. In various embodiments, a position on a reflective surface of an aspheric mirror may be separated by a distance in a range of from about 0.5 to about 5 mm or more from a position on an associated optical fiber toward which the fluorescent light is aimed.

In various embodiments, the aspheric mirrors 222, 226 can be separated by a distance 238 that enables unobstructed optical access to the ion trap die 202 by an optical device other than light sources positioned on the convex side of the aspheric mirrors to aim light beams in combination with the apertures thereof 224, 228. Such a distance 238 can, for example, enable unobstructed optical access by a light beam 239 from another light source (not shown) along the longitudinal axis of the ion trap die 202 and/or enable unobstructed optical access by a charge-coupled device (CCD) camera (not shown), among other possibilities.

The present disclosure can enable integration of aspheric mirrors (micromirrors) on a planar surface 204 of, in various embodiments, an intermediate die 108 and/or an interposer die 210 for improved addressing of ions in an ion trap die (e.g., an ion trap die having a plurality of ion locations) and/or improved addressing of distinct laser cooling and/or ion operation zones. In various embodiments, ion operations can include Raman cooling, state preparation, and/or gate operations. For example, Yb ions can be trapped using a 369 nanometer (nm) laser that is used for Doppler cooling and/or Raman cooling.

In various embodiments, ionization of Yb atoms can be performed at a location other than that used for laser cooling and/or ion operations. In some embodiments, repump lasers can provide a light beam axially along the horizontal axis of the ion trap from a location other than that used for the main laser cooling transition and/or ion operations.

Integrating the aspheric micromirrors near (e.g., having a reflective surface as close as 20 mm away from) a position of the ion trap die can enable tighter focusing of an excitation light beam and/or individual addressing of ion locations. Other possibilities can include multiple ion traps and/or ion trap dies positioned on a planar surface of a single interposer die and/or more intricate ion trap designs.

Integrating the optics for collection of the fluorescent light into and/or above the substantially planar surface 204 of the underlying intermediate die 108 and/or the interposer die 210 can enable collection of a higher percentage of the emitted fluorescent light, thus yielding a larger collection efficiency. Accordingly, the present disclosure describes curved (aspheric) mirrors integrated into the surface of the die to reflect fluorescent light by blocking a major portion of spherical space surrounding an ion that may emit fluorescent photons in random directions in order to increase coupling of captured and reflected fluorescent light to optical fibers.

The positioning of the ion locations and the optical fibers can be used to determine the configuration of the optics of the aspheric mirrors such that the fluorescent light is directed toward (e.g., aimed at) the optical fibers. Alternatively, the configuration of the optics of the aspheric mirrors can be used to determine the positioning of the ion locations and the optical fibers.

In various embodiments, the optical fibers can each have a designated portion configured to couple (e.g., by having an appropriate numerical aperture) with fluorescent light reflected from the various angles occupied by the aspheric mirrors. That is, an optical fiber can include a nub (not shown), for example, at an end of the optical fiber that is distal from the interposer die.

Depending upon the preferred implementation, such a nub can be above, at, or below the planar surface 204. In some embodiments with a plurality of optical fibers 234, 236, some of the nubs for each optical fiber can be below the planar surface 204, whereas other nubs can be at and/or above the planar surface 204.

Relative to the ion trap die, the aspheric mirrors can be integrated into the intermediate die and/or the interposer die in an ellipsoidal (semi-elliptical) orientation with a major axis aligned with (substantially parallel to) a longitudinal axis of the ion trap die. Fluorescent light emitted from a particular ion location can be reflected by a specifically contoured position on the reflective surface of an aspheric mirror such that the fluorescent light can be focused to a point and coupled to, for example, a position on a single-mode or multi-mode optical fiber placed above, at, or below the planar surface.

The collected fluorescent light can then be transmitted off-die through the intermediate die 108 and/or the interposer die 210 for amplification to, in some embodiments, a photomultiplier tube (PMT). Using aspherical mirrors described herein can enable focusing the fluorescent light from different ion locations along the ion trap die to separate optical fibers. An array of such optical fibers can enable differentiation between fluorescent light emitted from the different ion locations.

Furthermore, fluorescent light from multiple ion locations can be coupled simultaneously when an optical fiber, or a nub thereof, is placed at and/or within multiple image locations of the aspheric mirror. That is, an aspheric mirror can have multiple positions on its reflective surface each contoured (e.g., etched, deposited, molded, etc.) to focus fluorescent light emitted from a particular ion location, among a plurality of ion locations, toward a particular (designated) optical fiber.

Accordingly, a die-integrated aspheric mirror system, as just described, can include an ion trap die 202 including a plurality of ion locations 221 and a first aspheric mirror 222 having an ellipsoidal configuration (e.g., tri-axial) integrated with the ion trap die 202. A first light source (not shown) can be configured to promote emission of fluorescent light by excitation of at least one ion trapped in the plurality of ion locations 221.

For example, the first light source can be a laser tuned to produce coherent light at or around 369 nm to promote emission of fluorescent light by excitation of a single $Yb^+$ ion trapped in a single ion location 221 of the ion trap die 202. The first light source can, in various embodiments, be positioned distal to the first aspheric mirror 222 relative to the ion trap die 202.

The system can include a first number of optical fibers 234 positioned, in various embodiments, between the first aspheric mirror 222 and the ion trap die 202, where the number of optical fibers 234 can be configured, as described herein, to collect fluorescent light reflected by the first aspheric mirror 222 that was emitted from the plurality of ion locations 221. For example, the optical fibers 234 can be configured to collect the fluorescent light by the optical fibers having an appropriate numerical aperture given the configuration and/or positioning of the ion locations, the aspherical mirror, and/or the optical fibers.

The system can, in various embodiments, include a number of apertures 224-1, 224-2 in the first aspheric mirror 222. The first light source and the number of apertures 224-1, 224-2 can be configured to aim light to promote emission of fluorescent light from a particular ion location 221 of the plurality of ion locations. The number of apertures, the positioning, size, and/or shape of each of the apertures, and/or whether particular apertures include a lens can be determined based upon positioning of the first light source relative to the first aspheric mirror 222 and/or the number of apertures 224-1, 224-2 formed therethrough, in addition to the number of, distance to, and/or positioning of the plurality of ion locations 221.

The first light source can, in some embodiments, be a first laser movably positioned relative to the number of apertures 224-1, 224-2 on the distal side of the first aspheric mirror 222 relative to the ion trap die 202 in order to aim a light beam at a particular ion location 221. In some embodiments, the first light source can be mirrors, lenses, etc., that are associated with the first laser and that can be movably positioned relative to the number of apertures 224-1, 224-2 on the distal side of the first aspheric mirror 222 in order to aim a light beam at a particular ion location 221.

As described herein, the first aspheric mirror 222 can, in various embodiments, be configured with a number of image locations between the first aspheric mirror 222 and the ion trap die 202. As such, the first aspheric mirror 222 can be configured to focus fluorescent light emitted from the particular ion location 221 toward at least one designated optical fiber 234.

In some embodiments, a nub (not shown) can be formed on the at least one designated optical fiber 234 toward which the fluorescent light is focused. The nub can, in various embodiments, be configured to collect the fluorescent light reflected at various angles by the first aspheric mirror 222 by having a numerical aperture corresponding to the various angles to enable coupling with the reflected fluorescent light.

The system can, in various embodiments, include the ion trap die 202, the first aspheric mirror 222, and the first number of optical fibers 234 all being physically integrated with a substantially planar surface 204 of the underlying intermediate die 108 and/or the interposer die 210. In some embodiments, a longitudinal axis and a horizontal axis of the ion trap die 202 form a plane that can be substantially parallel with the substantially planar surface 204 of the underlying intermediate die 108 and/or the interposer die 210. Longitudinal axes of the first number of optical fibers 234 can, in some embodiments, be perpendicular to the substantially planar surface 204 of the underlying intermediate die 108 and/or the interposer die 210.

The first aspheric mirror 222 can, in various embodiments, be embedded into the substantially planar surface 204 of the underlying intermediate die 108 and/or the interposer die 210 along an axis of the first aspheric mirror 222 that can be substantially perpendicular to a principal axis of the first aspheric mirror 222. Accordingly, the ion trap die 202, the first aspheric mirror 222, the number of apertures 224-1, 224-2 in the first aspheric mirror 222, the first number of optical fibers 234, and/or the substantially planar surface 204 of the underlying intermediate die 108 and/or the interposer die 210 can, in various embodiments, be configured to enable unobstructed optical access to the plurality of ion locations 221 by light from the first light source.

The system can, in some embodiments, include a second aspheric mirror 226 having an ellipsoidal configuration integrated with the ion trap die 202. The second aspheric mirror 226 can be positioned on an opposite side of the ion trap die 202 relative to the first aspheric mirror 222.

In some embodiments, the system can include a second light source (not shown) configured to promote emission of fluorescent light by excitation of at least one ion trapped in the plurality of ion locations 221. The second light source can, in some embodiments, be a second laser movably positioned relative to the number of apertures 228-1, 228-2 on the distal side of the second aspheric mirror 226 relative to the ion trap die 202 in order to aim a light beam at a particular ion location 221. In some embodiments, the second light source can be mirrors and/or lenses, etc., that are associated with the first laser and/or the second laser and that can be movably positioned relative to the number of apertures 228-1, 228-2 on the distal side of the second aspheric mirror 226 in order to aim a light beam at a particular ion location 221 through the number of apertures 228-1, 228-2 of the second aspheric mirror 226.

The second light source can, in some embodiments, be tuned to produce resonant light at a particular frequency and/or wavelength to promote emission of fluorescent light by excitation of a single type of ion trapped in a single ion location 221 of the ion trap die 202. In some embodiments, the particular frequency and/or wavelength can be the same as or different from that of the first light source and/or the single type of ion can be the same as or different from that excited by the first light source.

The system can, in some embodiments, include a second number of optical fibers 236 positioned between the second aspheric mirror 226 and the ion trap die 202. The second number of optical fibers 236 can be configured, in various embodiments, to collect fluorescent light reflected by the second aspheric mirror 226 that was emitted from the plurality of ion locations 221.

The first aspheric mirror 222 and the second aspheric mirror 226 can each have a major axis positioned substantially parallel to the longitudinal axis of the ion trap die 202. The first aspheric mirror 222 and second aspheric mirror 226 can have opposing reflective surfaces. The first aspheric mirror 222 can have a first circumference and the second aspheric mirror 226 can have a second circumference, where the first and second circumferences can be the same or different.

The first circumference can, in various embodiments, have at least an arc thereof that is separated by a distance 238 from an opposing arc of the second circumference. In some embodiments, an entire circumference of the first aspheric mirror 222 can be separated from an entire circumference of the second aspheric mirror 226. The circumferences of the first aspheric mirror 222 and the second aspheric mirror 226 can be uniformly separated by the same distance 238 along the circumferences or the separation distance can vary at various points along the circumferences.

The distance 238 by which the first circumference and the second circumference are separated can enable unobstructed optical access to the ion trap die 202 by at least one of a CCD camera and/or a third light source. In various embodiments, the third light source can be configured to, along the longitudinal axis of the ion trap die 202, promote emission of fluorescent light by excitation of at least one ion trapped in the plurality of ion locations 221 and/or promote laser cooling of the at least one ion trapped in the plurality of ion locations 221, among other potential functions.

The aspheric mirrors and/or optical fibers described herein are suitable for implementation and/or integration into various ion trap architectures. Such attributes can contribute toward scalability to large arrays of ion traps by putting aspheric mirrors around each relevant zone, for example, to enable larger quantum informatics systems.

A system that utilizes die-integrated aspheric mirrors, as described herein, can yield a greater solid angle capture for fluorescent light, while not impeding an ability to address a particular ion location with excitation light sources (lasers) nor obstructing observation of the ion itself (e.g., with a CCD camera positioned to focus in a separation between two aspheric mirrors). In various embodiments, optical instruments (e.g., lasers, CCD cameras, etc.) can be placed inside and/or outside of a vacuum chamber (e.g., at around $10^{-8}$ pascals) enclosing a number of ion trap dies, aspheric mirrors, optical fibers, etc., as described herein.

Using microelectromechanical systems (MEMS) based techniques, structures can be etched into the fluorescent light collection system, or a die that is part of the system, that can enable the optical elements to be closely aligned by meeting strict tolerances of the MEMS. With the optical elements closely aligned and held securely in place via the MEMS-based structures being formed from and/or integrated with an associated die, the structure may be more robust to wear, impact, etc., than when, for instance, using bulk optics.

Figure 3:
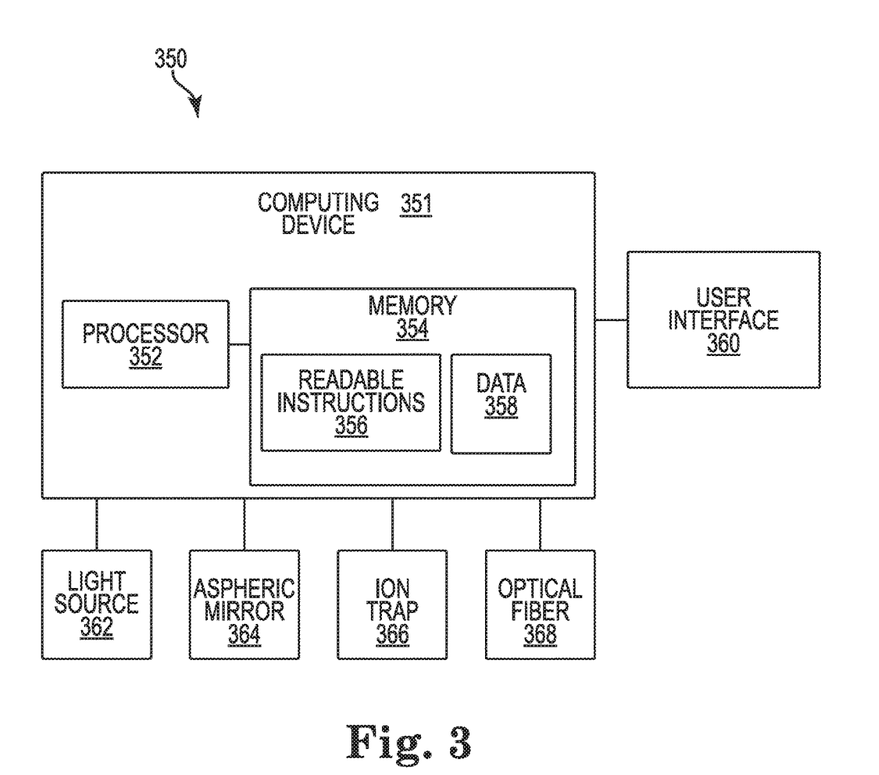
FIG. 3 illustrates a computing system that can be utilized in accordance with one or more embodiments of the present disclosure.

FIG. 3 illustrates a computing system 350 that can be utilized in accordance with one or more embodiments of the present disclosure. For instance, in various embodiments, the computing system 350 and/or other device having computing functionality can perform some or all of the functions described in the present disclosure.

For example, a computing device 351 (i.e., a device having computing functionality, as described herein) can include a computer-readable medium (CRM), integrated with and/or connected to a memory 354, in communication with a processing resource that includes one or more processors 352, which can function automatically and/or can be used by a user via a user interface 360 to accomplish a multitude of functions by executing computing device-readable instructions. The CRM can be in communication with a device that includes the processing resources. The device can be in communication with a tangible non-transitory CRM storing a set of computer-readable instructions (CRI) 356 executable by one or more of the processors 352, as described herein.

Data 358 can be stored in the CRM and/or the memory 354 and can be used by CRI 356 to accomplish computing tasks. In the embodiment of FIG. 3, the CRI 356 can be used to process data via fluorescent light (photons) input through a plurality of connected optical fibers 368. In some embodiments, the plurality of optical fibers 368 can be connected to the computing system 350 directly or indirectly via the interposer die and/or PMTs described herein.

The computing system 350 also can be connected to a number of light sources (e.g., lasers) 362 that, as described herein, can be utilized for ion operations and/or Doppler cooling, among other functions described herein or otherwise. The light sources 362 can, in various embodiments, be controlled via logic and/or executable CRI 356 executed by one or more processors 352.

In various embodiments, a light source 362 can be actuated to illuminate a particular location of an ion trap 366 a number of times (e.g., 2, 10, 25, etc.) during (e.g., within or separated by) a pre-determined timing sequence (e.g., 50 nanoseconds, 20 milliseconds, 1 minute, etc.). These characteristics and others can be determined automatically and/or set by a user, in various embodiments.

Example characteristics can include: positioning of the light source, positioning of mirrors, lenses, etc., associated with the light source, number of light source illuminations (pulses), frequency and/or wavelength of light (photons) emitted by the light source, timing sequence and/or duration, brightness of the illumination, among other characteristics. Such characteristics can be utilized in combination with configuration and/or positioning of a number of aspherical mirrors 364 to contribute to determination by the computing system 350 of, for example, a particular ion location from which the fluorescent light was emitted, as described herein.

Data collected by the computing system 350 can be stored in the memory 354 and can be utilized for execution of the embodiments of the present disclosure. In some embodiments, such data can be included in and/or compared to look-up tables (LUTs). The CRI 356 can be used for access of and/or storage in the LUTs and/or can utilize the LUTs for execution of the embodiments of the present disclosure.

The CRI 356 may be stored in remote memory managed by a server and represent an installation package that can be downloaded, installed, and/or executed. The computing system 350 and/or the computing device 351 can include additional memory resources, and processors 352 of the processing resources can be coupled to the additional memory resources.

Processors 352 can execute CRI that can be stored on an internal and/or an external non-transitory CRM. Processors 352 can execute CRI to perform various functions. For example, the processing resources can execute CRI to perform a number of functions.

A non-transitory CRM, as used herein, can include volatile and/or non-volatile memory. Volatile memory can include memory that depends upon power to store information, such as various types of dynamic random access memory (DRAM), among others.

Non-volatile memory can include memory that does not depend upon power to store information. Examples of non-volatile memory can include solid state media such as flash memory, electrically erasable programmable read-only memory (EEPROM), phase change random access memory (PCRAM), magnetic memory such as a hard disk, tape drives, floppy disk, and/or tape memory, optical discs, digital versatile discs (DVD), Blu-ray discs (BD), compact discs (CD), and/or a solid state drive (SSD), etc., as well as other types of computer-readable media.

The non-transitory CRM can also include distributed storage media. For example, the CRM can be distributed among various locations. The non-transitory CRM can be integral, or communicatively coupled, to a computing device, in a wired and/or a wireless manner. For example, the non-transitory CRM can be an internal memory, a portable memory, a portable disk, and/or a memory associated with another computing resource (e.g., enabling CRIs to be transferred and/or executed across a network such as the Internet).

The CRM can be in communication with the processing resources via a communication path. The communication path can be local or remote to a machine (e.g., a computer) associated with the processing resources.

Examples of a local communication path can include an electronic bus internal to a machine (e.g., a computer) where the CRM is one of volatile, non-volatile, fixed, and/or removable storage medium in communication with the processing resources via the electronic bus. Examples of such electronic buses can include Industry Standard Architecture (ISA), Peripheral Component Interconnect (PCI), Advanced Technology Attachment (ATA), Small Computer System Interface (SCSI), Universal Serial Bus (USB), among other types of electronic buses and variants thereof.

The communication path can be such that the CRM is remote from the processing resources such as in a network relationship between the CRM and the processing resources. That is, the communication path can be a network relationship. Examples of such a network relationship can include a local area network (LAN), wide area network (WAN), personal area network (PAN), and/or the Internet, among others. In such examples, the CRM can be associated with a first computing device and the processing resources can be associated with a second computing device.

Accordingly, a die-integrated aspheric mirror system, as described in the present disclosure, can be implemented in combination with a computing system, as just described. Such a combination can, in various embodiments, include an ion trap die, a first aspheric mirror integrated with the ion trap die, a light source configured to promote emission of fluorescent light by aimed excitation of a plurality of ions each trapped in one of a plurality of ion locations, and/or a first plurality of optical fibers positioned between the first aspheric mirror and the ion trap die to collect fluorescent light.

Such a combination also can, in various embodiments, include a processor and memory having executable instructions to be executed by the processor. The instructions can, in some embodiments, be executed to determine a particular ion location from which the fluorescent light was emitted by each of the first plurality of optical fibers being positioned to collect fluorescent light focused thereon by the first aspheric mirror. Such a system can, in some embodiments, be implemented for quantum informatics processing.

In various embodiments, to determine the particular ion location can include a focus of the fluorescent light on a particular optical fiber determined by an appropriate (e.g., predetermined) combination of a configuration of a reflective surface of the first aspheric mirror and angular orientations to the reflective surface of a position of the particular optical fiber and a position of the particular ion location.

The system can, in various embodiments, include a plurality of apertures in the first aspheric mirror. The light source and the plurality of apertures can be configured to simultaneously aim light to promote substantially simultaneous emission of fluorescent light from the plurality of ion locations. The memory of the computing system can further include executable instructions to be executed by the processor to determine the particular ion locations from which the fluorescent light was substantially simultaneously emitted.

The system can, in various embodiments, include a second aspheric mirror and a second plurality of optical fibers integrated on an opposite side of the ion trap die relative to the first aspheric mirror. Such a configuration can be utilized to increase a solid angle capture of the fluorescent light in order to improve determination of the particular ion location from which the fluorescent light was emitted.

As used herein, "logic" is an alternative or additional processing resource to execute the actions and/or functions, etc., described herein, which includes hardware (e.g., various forms of transistor logic, application specific integrated circuits (ASICs), etc.), as opposed to computer executable instructions (e.g., software, firmware, etc.) stored in memory and executable by a processor, such as a microprocessor.

The embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure. It is also to be understood that the terminology used herein is for the purpose of describing particular embodiments only, and is not intended to be limiting.

As will be appreciated, elements shown in the various embodiments herein can be added, exchanged, combined, and/or eliminated so as to provide a number of additional embodiments of the present disclosure. The proportion and/or the relative scale of the elements provided in the figures are intended to illustrate the embodiments of the present disclosure, and should not be taken in a limiting sense.

As used herein, the singular forms "a", "an", and "the" include singular and plural referents, unless the context clearly dictates otherwise, as do "a number of", "at least one", and "one or more". For example, "a number of ion locations" can refer to one or more ion locations. Furthermore, the words "can" and "may" are used throughout this application in a permissive sense (i.e., having the potential to, being able to), not in a mandatory sense (i.e., must).

The term "include", and derivations thereof, mean "including, but not limited to." The term "integrated", and derivations thereof, mean two or more physical entities directly connected to each other or mutually connected via another physical entity.

The term "die" is used herein to mean a block of semiconducting material (e.g., electronic-grade silicon and/or another semiconductor) on which and/or in which a particular functionality (e.g., circuitry) can be fabricated. The terms "coupled" and "coupling" mean to be directly or indirectly connected in light (e.g., photon) uptake or transmission (e.g., an optical fiber having a numerical aperture appropriate for uptake of light). The term "wire bond" is used for convenience herein and is inclusive of various techniques of connecting electrical leads, which can include thermosonic wire bonding, for making interconnections between electrical leads and an integrated circuit or other semiconductor device and its packaging during fabrication.

Although specific embodiments have been illustrated and described herein, those of ordinary skill in the art will appreciate that an arrangement calculated to achieve the same techniques can be substituted for the specific embodiments shown. This disclosure is intended to cover any and all adaptations and/or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. In the foregoing Detailed Description, various features are grouped together in example embodiments illustrated in the figures for the purpose of streamlining the disclosure.

This method of disclosure is not to be interpreted as reflecting an intention that the embodiments of the disclosure require more features than are expressly recited in each claim. Rather, inventive subject matter lies in less than all features of a single disclosed embodiment. Therefore, the scope of various embodiments of the disclosure should be determined with reference to the appended claims, along with the full range of equivalents to which such claims are entitled.

What is claimed:

1. An apparatus, comprising:
an ion trap die comprising a plurality of separate ion locations each configured to separately trap an ion in a potential well.

2. The apparatus of claim 1, wherein:
the ion trap die comprises a longitudinal axis; and
the apparatus further comprises an aspheric mirror configured to be physically integrated with the ion trap die such that a principal axis of the aspheric mirror is substantially aligned with and perpendicular to the longitudinal axis of the ion trap die.

3. The apparatus of claim 1, wherein:
the ion trap die comprises a horizontal axis; and
the apparatus further comprises an aspheric mirror configured to be physically integrated with the ion trap die such that a principal axis of the aspheric mirror is substantially aligned with the horizontal axis of the ion trap die.

4. The apparatus of claim 1, further comprising:
an aspheric mirror physically integrated with the ion trap die; and
wherein the aspheric mirror is formed with an ellipsoidal configuration.

5. The apparatus of claim 4, wherein:
a major axis of the ellipsoidal configuration is substantially parallel to a longitudinal axis of the ion trap die; and
a minor axis of the ellipsoidal configuration is substantially perpendicular to a horizontal axis of the ion trap die.

6. The apparatus of claim 1, wherein the ion trap die and an aspheric mirror are both physically integrated with a substantially planar surface of a substrate die.

7. A die-integrated aspheric mirror system, comprising:
an ion trap die comprising a plurality of separate ion locations each configured to separately trap an ion in a potential well;
a first aspheric mirror physically integrated with the ion trap die; and
a first light source configured to promote emission of light by excitation of at least one ion trapped in the plurality of separate ion locations, wherein the first light source is positioned distal to the first aspheric mirror relative to the ion trap die.

8. The system of claim 7, further comprising a number of apertures in the first aspheric mirror, wherein the first light source and the number of apertures are configured to aim light to promote emission of light from a particular ion location of the plurality of separate ion locations.

9. The system of claim 7, wherein the first aspheric mirror is configured with a number of image locations between the first aspheric mirror and the ion trap die.

10. The system of claim 7, wherein the first aspheric mirror is configured to focus light emitted from a particular ion location of the plurality of separate ion locations toward at least one designated optical fiber.

11. The system of claim 10, further comprising a nub on the at least one designated optical fiber toward which the light is focused,
wherein the nub is configured to collect the light reflected at various angles by the first aspheric mirror having a numerical aperture corresponding to the various angles to enable coupling with the reflected light.

12. The system of claim 7, further comprising:
the ion trap die, the first aspheric mirror, and a first number of optical fibers all being physically integrated with a substantially planar surface of an underlying interposer die;
wherein a longitudinal axis and a horizontal axis of the ion trap die forms a plane that is substantially parallel with the substantially planar surface of the underlying interposer die;
wherein longitudinal axes of the first number of optical fibers are perpendicular to the substantially planar surface of the underlying interposer die;
wherein the first aspheric mirror is embedded into the substantially planar surface of the underlying interposer die along an axis substantially perpendicular to a principal axis of the first aspheric mirror; and
wherein the ion trap die, the first aspheric mirror, a number of apertures in the first aspheric mirror, the first number of optical fibers, and the substantially planar surface of the underlying interposer die are configured to enable unobstructed optical access to the plurality of separate ion locations by light from the first light source.

13. The system of claim 7, further comprising:
a second aspheric mirror physically integrated with the ion trap die, wherein the second aspheric mirror is on an opposite side of the ion trap die relative to the first aspheric mirror;
a second light source configured to promote emission of light by excitation of at least one ion trapped in the plurality of separate ion locations; and
a second number of optical fibers positioned between the second aspheric mirror and the ion trap die, wherein the second number of optical fibers is configured to collect light reflected by the second aspheric mirror that was emitted from the plurality of separate ion locations.

14. The system of claim 13, wherein:
the first aspheric mirror and the second aspheric mirror each have a major axis positioned substantially parallel to a longitudinal axis of the ion trap die, wherein the first aspheric mirror and second aspheric mirror have opposing reflective surfaces; and
the first aspheric mirror has a first circumference and the second aspheric mirror has a second circumference, wherein the first circumference has at least an arc thereof that is separated by a distance from an opposing arc of the second circumference.

15. The system of claim 14, wherein the distance by which the first circumference and the second circumference are separated enables unobstructed optical access to the ion trap die by at least one of a charge-coupled device camera and a third light source.

16. A die-integrated aspheric mirror system, comprising:
an ion trap die comprising a plurality of separate ion locations each configured to separately trap an ion in a potential well;
a first aspheric mirror physically integrated with the ion trap die; and
a first plurality of optical fibers positioned between the first aspheric mirror and the ion trap die to collect light.

17. The system of claim 16, wherein:
determination of a particular ion location comprises a focus of light on a particular optical fiber determined by an appropriate combination of a configuration of a reflective surface of the first aspheric mirror and angular orientations to the reflective surface of a position of the particular optical fiber and a position of the particular ion location.

18. The system of claim 16, further comprising:
a plurality of apertures in the first aspheric mirror, wherein a light source and the plurality of apertures are configured to simultaneously aim light to promote substantially simultaneous emission of light from the plurality of separate ion locations; and
memory having executable instructions to be executed by a processor:
determine a particular ion location from which the light was emitted by each of the first plurality of optical fibers being positioned to collect light focused thereon by the first aspheric mirror; and
to determine the particular ion locations from which the light was substantially simultaneously emitted.

19. The system of claim 16, further comprising:
a second aspheric mirror and a second plurality of optical fibers physically integrated on an opposite side of the ion trap die relative to the first aspheric mirror to increase a solid angle capture of the light in order to improve determination of the particular ion location from which the light was emitted.

20. The system of claim 16, wherein the system is implemented to enable quantum informatics processing.

* * * * *